United States Patent [19]

Spector

[11] Patent Number: 4,728,212

[45] Date of Patent: Mar. 1, 1988

[54] NOVELTY WRITING PEN

[76] Inventor: Donald Spector, 380 Mountain Rd., Union City, N.J. 07087

[21] Appl. No.: 264,808

[22] Filed: May 18, 1981

Related U.S. Application Data

[63] Continuation-in-part of Ser. No. 70,512, Aug. 28, 1979, Pat. No. 4,283,011.

[51] Int. Cl.$^4$ .......................... B43K 7/00; B43K 23/00; B43K 29/00
[52] U.S. Cl. ........................................ 401/88; D19/41; D19/42; 40/334; 401/195; 401/209
[58] Field of Search ....................... D19/41, 42, 43, 45, D19/57; 40/334; 401/88, 6, 195, 209, 52, 196, 213, 202; 239/34, 60, 55, 54, 53; 106/20

[56] References Cited

U.S. PATENT DOCUMENTS

| | | | |
|---|---|---|---|
| D. 222,306 | 10/1971 | Fever | D19/42 |
| 1,647,536 | 11/1927 | Miller | 401/88 |
| 3,457,014 | 7/1969 | Ward | 401/202 X |
| 3,888,416 | 6/1975 | Lin | 401/195 X |
| 4,283,011 | 8/1981 | Spector | 239/36 |

FOREIGN PATENT DOCUMENTS

| | | | |
|---|---|---|---|
| 715967 | 12/1931 | France | 106/20 |
| 919443 | 3/1947 | France | 106/20 |

Primary Examiner—Steven A. Bratlie
Attorney, Agent, or Firm—Michael Ebert

[57] ABSTRACT

A novelty writing pen constituted by a standard pen having an ink reservoir encased in a sheath and terminating in a writing tip projecting from one end of the sheath, and a molded body configured to represent a familiar object such as a fruit emitting a characteristic odor, the body having a bore therein to receive at least the upper section of the sheath so that the body is carried by the pen. The ink in the pen incorporates an odor-producing component which is compatible therewith. When the pen is put to use, this component causes the surface written on by the pen to exude an odor simulating that of the object carried thereby.

3 Claims, 5 Drawing Figures

U.S. Patent    Mar. 1, 1988    4,728,212
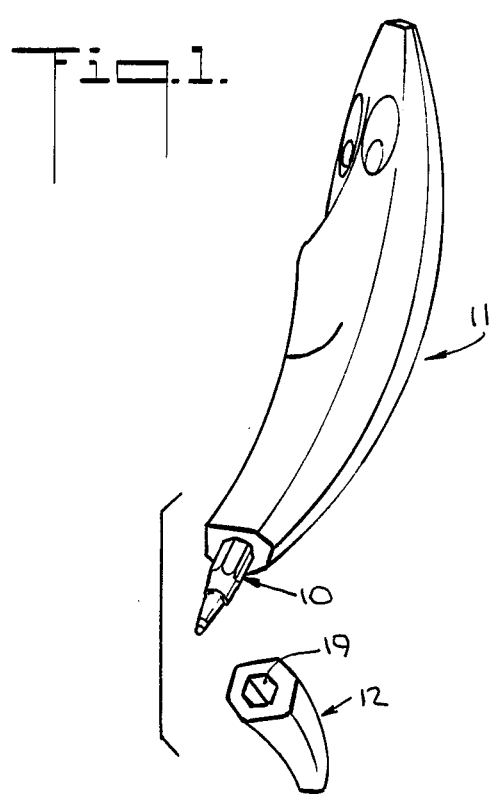
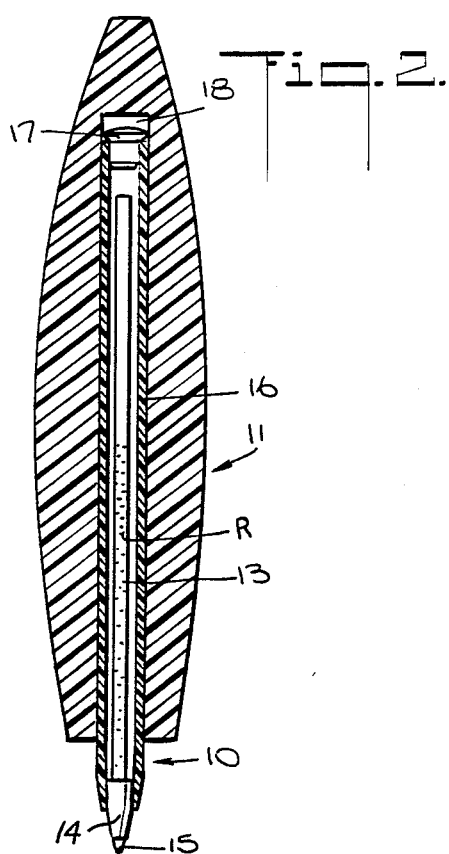
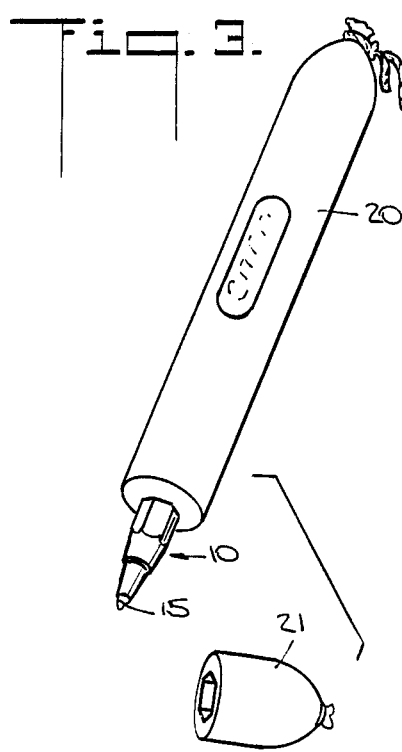
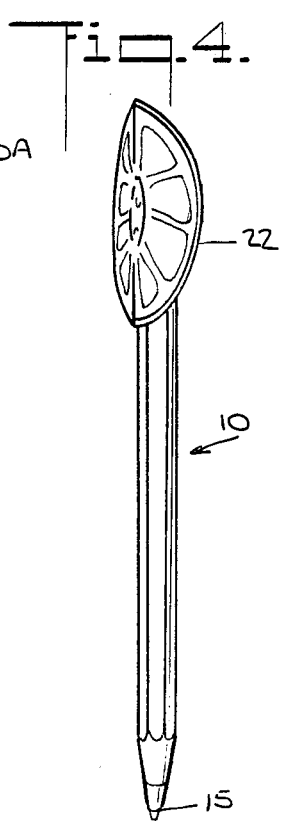
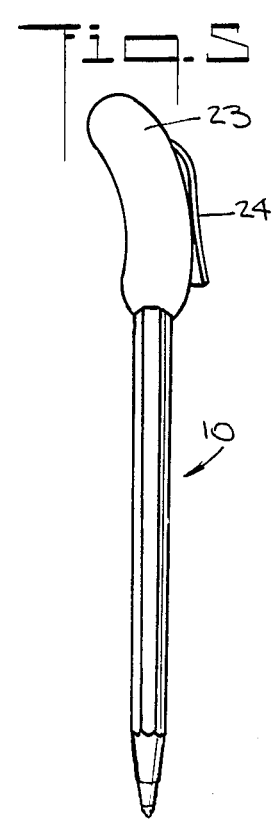

NOVELTY WRITING PEN

BACKGROUND OF INVENTION

This invention relates generally to novelty writing pens, and more particularly to a pen which presents the appearance of a fruit or other familiar object having a characteristic odor and whose writing ink incorporates as a component thereof a volatile oil or other scent-producing liquid, so that when the user writes with the pen, the resultant smell exuded from the writing surface suggests the object's odor.

A ballpoint pen is a writing instrument in which a tiny ball housed in a socket at the tip transfers ink from a tubular reservoir onto the writing surface. The ink is a viscous fluid containing a dye which may be oil or spirit-soluble. The ball, which is usually made of steel and in some cases of synthetic sapphire, when not moving, acts to seal the end of the ink reservoir, thereby preventing the ink from drying out. In some instances, the pen makes use of a felt tip to obtain a broader writing stroke.

In some commercially-available pens, the tubular ink reservoir which terminates in a tip is a separable unit which may be replaced when the ink is exhausted. In other instances, the reservoir is locked into the sheath of the pen, so that one simply disposes of the pen when the ink is exhausted. The concern of the present invention is with standard pen of the above type which employ a viscous ink as distinguished from relatively-expensive fountain pens which make use of non-viscous inks and flexible pen points.

A novelty writing pen in accordance with the invention is adapted when used as a writing instrument to exude a distinctive odor which simulates the natural aroma of a familiar odoriferous object, such as a fruit or a sausage.

As used herein, the terms "aroma" and "scent" are not limited to pleasant or savory fragrances but encompass all known odors, whether agreeable or offensive, which are characteristic of odoriferous objects. The term "odoriferous object" includes not only fruits and other forms, such as frankfurters, but animals such as skunks, which give off easily recognized and distinctive odors.

Aroma-producing chemicals are incorporated in numerous products on the market: cosmetics, soaps, scented papers, tobacco and many types of household products. Though most chemical aromas are created with a pleasing effect in mind, other functions are served thereby. Thus it is the common practice to add to an otherwise odorless fuel gas which is toxic, a pungent odor which functions to warn those who sense this odor that a gas line leak exists.

It is now possible to chemically-synthesize aromas to set moods, associations and reactions, in addition to these aromas that are aesthetically pleasing but otherwise without meaning.

Volatile oils and other scent-producing substances used in perfumes were originally derived from natural substances. However, once the chemical composition of any of these substances is identified, the same composition, however complex, can in most cases now be duplicated by organic synthesis. Representative of such duplications are the following familiar scents and their related compounds:

Apple—Geranyl
Lemon—Citral
Pine—Bornyl Isovalerate
Strawberry—Ethylmethylphenyl glycidate.

In my above-identified copending application, there is disclosed an aroma-dispensing sticker that is attachable to an article of clothing. The sticker includes an appliqué sheet contoured to represent an odoriferous object such as a flower, the scent dispensed by the sticker simulating the characteristic natural odor of the flower. The prior art made of record in this copending application, which has now issued as U.S. Pat. No. 4,283,011, is therefore also pertinent to the present invention which deals with an odor-generating writing pen having the appearance of an odoriferous object.

SUMMARY OF INVENTION

In view of the foregoing, the main object of this invention is to provide a novelty writing pen which has the appearance of an odoriferous object, the ink in the pen incorporating an odor-producing component which is compatible with the ink and which, when the pen is put to use, causes the surface written on to exude an odor simulating the characteristic odor of the object.

More particularly, it is an object of this invention to provide a novelty pen which makes use of a standard ball point or felt tip pen that is insertable into a molded body configured to represent the odoriferous object.

Also an object of the invention is to provide a novelty pen of the above type in which the configured body is in two parts; one serving to house the pen except for the tip section, and the other serving to cap the tip section.

Briefly stated, these objects are accomplished in a novelty writing pen constituted by a standard pen having an ink reservoir encased in a sheath and terminating in a writing tip projecting from one end of the sheath, and a molded body configured to represent a familiar object, such as a fruit, having a characteristic odor, the body having a bore therein to receive at least the upper section of the sheath so that the body is carried by the pen. The ink in the pen incorporates an odor-producing component which is compatible therewith and which, when the pen is put to use, causes the surface written on to exude an odor simulating that of the object.

OUTLINE OF DRAWINGS

For a better understanding of the invention as well as other objects and further features thereof, reference is made to the following detailed description to be read in conjunction with the accompanying drawings, wherein:

FIG. 1 illustrates, in perspective, a novelty pen in accordance with the invention in which the two-part molded body is configured to represent a banana;

FIG. 2 is a section taken through the novelty pen, the lower part of the body being omitted;

FIG. 3 shows a novelty pen whose two-part body is configured to represent a sausage;

FIG. 4 shows a novelty pen whose one part body which is attached to the upper section of the pen is configured to represent an orange slice; and FIG. 5 illustrates a novelty pen having a frankfurter-like attachment that also functions as a clip.

DESCRIPTION OF INVENTION

First Embodiment:

Referring now to FIGS. 1 and 2, there is shown a novelty pen constituted by a standard ball point pen, generally designated by numeral 10, and a molded body formed by separable parts 11 and 12 which when together assume the form of a banana having a humanoid appearance.

Pen 10, which is of conventional design, includes a tubular plastic reservoir R containing a supply of viscous ink 13, the lower end of the reservoir being coupled to a metal socket 14 whose tip houses a ball point 15. The reservoir is supported concentrically by the socket within a sheath 16 whose upper end is sealed by a cap 17.

The ink supply 13 incorporates therein a volatile oil or other component which is compatible with the ink and whose composition is such that it produces a banana-like odor. As pointed out in the background section, it is possible by organic synthesis to recreate virtually any natural odor, the amount of odor-producing oil used for this purpose being such as to create the desired odor without, however, interfering with the normal properties of the viscous ink.

The upper part 11 of tha banana-like body 11 has a longitudinally extending bore 18 therein dimensioned to receive and frictionally engage the entire pen 10 except for its tip section which projects axially from the bore, so that one can write with the pen by grasping body part 11. The lower and removable part 12 of the body is provided with a bore 19 to receive and frictionally engage the tip section of the pen; so that when part 12 is in place, the pen is entirely concealed, and to all appearances, the product is simply a fanciful replica of a banana.

The body is preferably molded of a resilient, synthetic, thermoplastic material such as polyvinyl chloride or polypropylene. When one writes with this novelty pen, the ink on the writing surface then exudes an odor simulating that of a banana. While a ballpoint pen is shown, in practice the pen may be a standard felt tip pen or any other type, other than a fountain pen.

Other Embodiments:

The novelty pen illustrated in FIG. 3 has the appearance of a salami or sausage, the sausage-like body being composed of an upper part 20 having a string 20A attached to the end thereof to imitate the string usually used to knot the end of a sausage casing. The sausage-like body is completed by a removable body part 21 which serves to cap the tip section of the pen when the pen is not in use. In this instance, the ink in the sausage-like novelty pen includes a component which exudes the meat-like odor of a sausage.

FIG. 4 shows a novelty pen composed of a standard ballpoint pen 10 in which the one part molded body 22 is configured to represent an orange slice, this body being attached to the upper section of the pen. In this instance, the ink includes an odor-producing component that exudes an orange-simulating smell.

In FIG. 5, the molded body 23 attached to the upper end of the pen simulates a small frankfurter, and the ink includes a component producing a frankfurter-like smell. The body further includes a clip 24 which is integral therewith, so that the novelty pen may be clipped onto a pocket.

While there have been shown and described preferred embodiments of a novelty writing pen in accordance with the invention, it will be appreciatad that many changes and modifications may be made therein without, however, departing from the essential spirit thereof. Thus instead of objects in the form of foods as illustrated herein, the body attached to the pen may be configured as an animal such as a skunk, the ink then exuding the characteristic odor of this animal. For promotional purposes, say in connection with a perfume which comes in a distinctive bottle, the object attached to the pen may be given the configuration of the bottle, and the ink may then include as a component the actual perfume.

I claim:

1. A novelty pen comprising:
   A. a standard writing pen having a tubular ink reservoir encased in a sheath and terminating in a writing tip projecting from one end of the sheath;
   B. a supply of ink in said reservoir incorporating an odor-producing component compatible with the ink, the odor simulating the characteristic smell of an odor-producing object whereby when the user writes on a surface with the pen, the inked surface exudes the odor of said object; and
   C. a molded body having a bore therein to receive at least the upper section of the pen, so that the body is carried by the pen, the body having a configuration representing the object whose odor is exuded by the ink whereby the user appears to be writing with the odor-producing object, said body, being composed of two parts which together represent the object, the upper part being carried by the upper section of the pen, the lower part being carried by the tip section of the pen and being removable therefrom.

2. A novelty pen as set forth in claim 1, wherein said body represents a banana.

3. A novelty pen as set forth in claim 1, wherein said body represents a sausage.

* * * * *